(12) United States Patent
Ovadia

(10) Patent No.: US 7,359,042 B2
(45) Date of Patent: Apr. 15, 2008

(54) INSPECTION SYSTEM FOR LIMITED ACCESS SPACES

(75) Inventor: Yuval Ovadia, Kibbutz Yagur (IL)

(73) Assignee: S.T.I. Security Technology Integration Ltd, Shefayim (IL)

( * ) Notice: Subject to any disclaimer, the term of this patent is extended or adjusted under 35 U.S.C. 154(b) by 285 days.

(21) Appl. No.: 10/252,040

(22) Filed: Sep. 23, 2002

(65) Prior Publication Data

US 2004/0057042 A1    Mar. 25, 2004

(51) Int. Cl.
*G01N 21/00* (2006.01)
(52) U.S. Cl. ............ 356/237.1; 356/318; 356/73; 378/88; 438/143
(58) Field of Classification Search .. 356/237.1–237.5, 356/394, 601–623; 348/148, 143
See application file for complete search history.

(56) References Cited

U.S. PATENT DOCUMENTS

| | | | | |
|---|---|---|---|---|
| 3,873,837 A * | 3/1975 | Palermo, Jr. | ................. | 378/61 |
| 4,585,350 A * | 4/1986 | Pryor | .......................... | 356/625 |
| 4,652,758 A * | 3/1987 | Barfod | .................. | 250/363.04 |
| 4,989,981 A * | 2/1991 | Kawamura et al. | ......... | 356/394 |
| 5,274,549 A * | 12/1993 | Almasi | ........................ | 600/526 |
| 5,295,073 A * | 3/1994 | Celette | ......................... | 701/35 |
| 5,376,796 A * | 12/1994 | Chan et al. | ............ | 250/363.04 |
| 5,394,654 A * | 3/1995 | Shimbara et al. | ............... | 451/6 |
| 5,477,371 A * | 12/1995 | Shafir | .......................... | 359/201 |
| 5,521,707 A * | 5/1996 | Castore et al. | .............. | 356/394 |
| 5,625,197 A * | 4/1997 | Shimbara | ............... | 250/559.22 |
| 5,671,055 A * | 9/1997 | Whittlesey et al. | ......... | 356/602 |
| 6,249,567 B1 | 6/2001 | Rothschild et al. | | |
| 6,320,654 B1* | 11/2001 | Alders et al. | ............. | 356/237.2 |
| 6,407,818 B1* | 6/2002 | Whitehouse | ................. | 356/627 |
| 6,417,919 B1* | 7/2002 | Hewitt et al. | ............. | 356/237.1 |
| 6,600,168 B1* | 7/2003 | Geng | ..................... | 250/559.22 |
| 7,030,753 B2* | 4/2006 | Hentz et al. | ................. | 340/531 |
| 2004/0165750 A1* | 8/2004 | Chew | .......................... | 382/105 |

FOREIGN PATENT DOCUMENTS

| | | | |
|---|---|---|---|
| GB | 2258321 A | * | 2/1993 |
| JP | 404001506 A | * | 1/1992 |
| JP | 11313311 A | * | 11/1999 |

* cited by examiner

*Primary Examiner*—Hoa Q. Pham
(74) *Attorney, Agent, or Firm*—Pearl Cohen Zedek Latzer, LLP

(57) ABSTRACT

A limited access space inspection system comprising: an imaging device for imaging a region in the limited access space, a mounting for mounting the imaging device to scan about the limited access space and a scanning control unit, associated with the imaging device, for controlling the imaging device to scan about the limited access space. The device is particularly useful for improving by automation, security checks customs checks and safety checks involving such awkward to access spaces.

25 Claims, 6 Drawing Sheets

INSPECTION SYSTEM FOR LIMITED ACCESS SPACES

FIELD AND BACKGROUND OF THE INVENTION

The present invention relate, to an inspection system for limited access spaces and, more particularly, but not exclusively to a vehicle inspection system suitable for inspection of parts of vehicles that are awkward to inspect easily.

Vehicle underside inspection is necessary for several reasons, one being to provide security, a second being for safety and a third being for contraband detection, by customs inspectors and the like. On the security side, undersides of vehicles may have concealed explosive devices Of particular concern is the possibility of concealing an explosive device on the underside of a fuel tanker, which device is timed or controlled to explode when the tanker is inside a fuel distribution depot. Carrying out detailed manual inspections of the undersides of each tanker entering a fuel depot is both time and labor consuming On the safety side, the underside of the vehicle may conceal a mechanical flaw, the early detection of which may prevent an accident. In a garage or workshop a car is generally jacked up or placed on a ramp. Larger vehicles are placed on ramps or are driven over inspection pits. However, outside the garage environment, inspection of the underside of a vehicle is difficult. Contraband detection at borders by customs officials is often based on spot checks since customs very rarely have the resources to inspect every passing vehicle. Any means of allowing a more detailed inspection in a smaller time frame would be welcome.

Security checks for entry into government buildings and the like are typically carried out using a mirror on the end of a pole, which is inserted under the vehicle. However, without illumination it is difficult to see much detail and even with illumination, an explosive device can be concealed in a spot that is awkward to view using the mirror. Furthermore such a mirror is very unlikely to spot hairline cracks, which are usually the first signs of dangerous mechanical faults. It is impractical to install inspection pits at all places where regular vehicle checks are desirable.

US Pat. No. 6,249,567 to Rothschild et al discloses an inspection system for inspecting a vehicle moving at a grade of travel over a surface and for detecting material disposed within or on the underside of the vehicle. The system has a source for providing a generally upward or downward pointing beam of penetrating radiation of specified cross-section so as to illuminate vehicles driven above or below the source of radiation. A detector arrangement, disposed below the grade of travel, detects radiation from the beam scattered by any material disposed on the underside of the moving vehicle and generates a scattered radiation signal that may be used for characterizing the material disposed on the underside on the vehicle. Similarly, a detector arrangement disposed above the vehicle generates a scattered radiation signal that may be used for characterizing the material disposed within the vehicle. The system however sits at a single location, requiring the vehicle to move during inspection. It cannot independently scan the vehicle underside. Furthermore, the main detection function of the system is based on x-rays, since a principle intention is to scan for the internal contents of the vehicle.

There is thus a widely recognized need for, and it would be highly advantageous to have, a vehicle inspection system devoid of the above limitations.

SUMMARY OF THE INVENTION

According to one aspect of the present invention there is provided a limited access space inspection system comprising:

an imaging device for imaging a region in said limited access space, a mounting for mounting said imaging device to be scannable about said limited access space and a scanning control unit, associated with said imaging device, for controlling said imaging device to scan about said limited access space.

The system preferably comprises a protective housing for protecting said imaging device from the environment by interposing between at least said imaging device and said region to be imaged.

Preferably, said protective housing comprises a transparent region located between said imaging device and said region to be imaged.

Preferably, said transparent region comprises laminated glass.

Preferably, said laminated glass is triplex laminated glass.

Preferably, said mounting is a floor mounting for mounting said imaging device at floor level.

Preferably, said mounting comprises a camera track for movably bearing said imaging device.

Preferably, said mounting comprises guide tracks for guiding a vehicle thereover, an underside of said vehicle thereby forming said limited access space.

Preferably, said mounting is a flush floor mounting for insertion into a floor cavity.

The system preferably comprises an illumination source for providing illumination to said limited access space.

The system preferably comprises a display output for providing a display signal.

Preferably, an image processor is located between said imaging device and said display output to process images from said imaging device prior to output.

Preferably, said image processor is operable to compare a current image of said region with a previous image to detect differences therebetween.

Preferably, said imaging device is linearly movable along said camera track, is rotatable about an axis perpendicular to said track, and is further rotatable about an axis parallel to said track.

Preferably, said scanning control unit is controllable by at least one of direct user input and by preprogramming, to scan said imaging device about said limited access space.

According to a second aspect of the present invention there is provided a vehicle underside inspection system comprising:

a floor mounted track, an imaging device mounted on said floor track to be linearly movable along said floor track, and a display output, associated with said imaging device, for providing a display signal of output of said imaging device.

The system preferably comprises a scanning controller for controlling said imaging device to scan an imaging region over said floor track.

Preferably, said imaging device is rotatable about an axis perpendicular to said floor track, and is further rotatable about an axis parallel to said floor track.

Preferably, said floor mounted track comprises an outer housing and wherein said imaging device is sealed within said outer housing.

According to a third aspect of the present invention there is provided a method of scanning a limited access space, the method comprising:

interpolating a linear track into said space, said linear track having an imaging device movably mounted thereon, and moving said imaging device along said track, thereby to scan said space.

Preferably, said interpolating said linear track into said space comprises locating a vehicle over said track, an underside of said vehicle forming said limited access space.

The method preferably further comprises interpolating an illumination source into said space.

Preferably, said linear track is flush with a floor.

Unless otherwise defined, all technical and scientific terms used herein have the same meaning as commonly understood by one of ordinary skill in the art to which this invention belongs. The materials, methods, and examples provided herein are illustrative only and not intended to be limiting.

Implementation of the method and system of the present invention involves performing or completing certain selected tasks or steps such as scanning manually, automatically, or a combination thereof. Moreover, according to actual instrumentation and equipment of preferred embodiments of the method and system of the present invention several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system or the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail it is stressed that the particulars shown are by way of example and for purposes of illustrative discussion of the preferred embodiments of the present invention only, and are presented in the cause of providing what is believed to be the most useful and readily understood description of the principles and conceptual aspects of the invention in this regard, no attempt is made to show structural details of the invention in more detail than is necessary for a fundamental understanding Of the invention, the description taken with the drawings making apparent to those skilled in the art how the several forms of the invention may be embodied in practice.

In the drawings.

DESCRIPTION OF THE PREFERRED EMBODIMENTS

Figure 1:
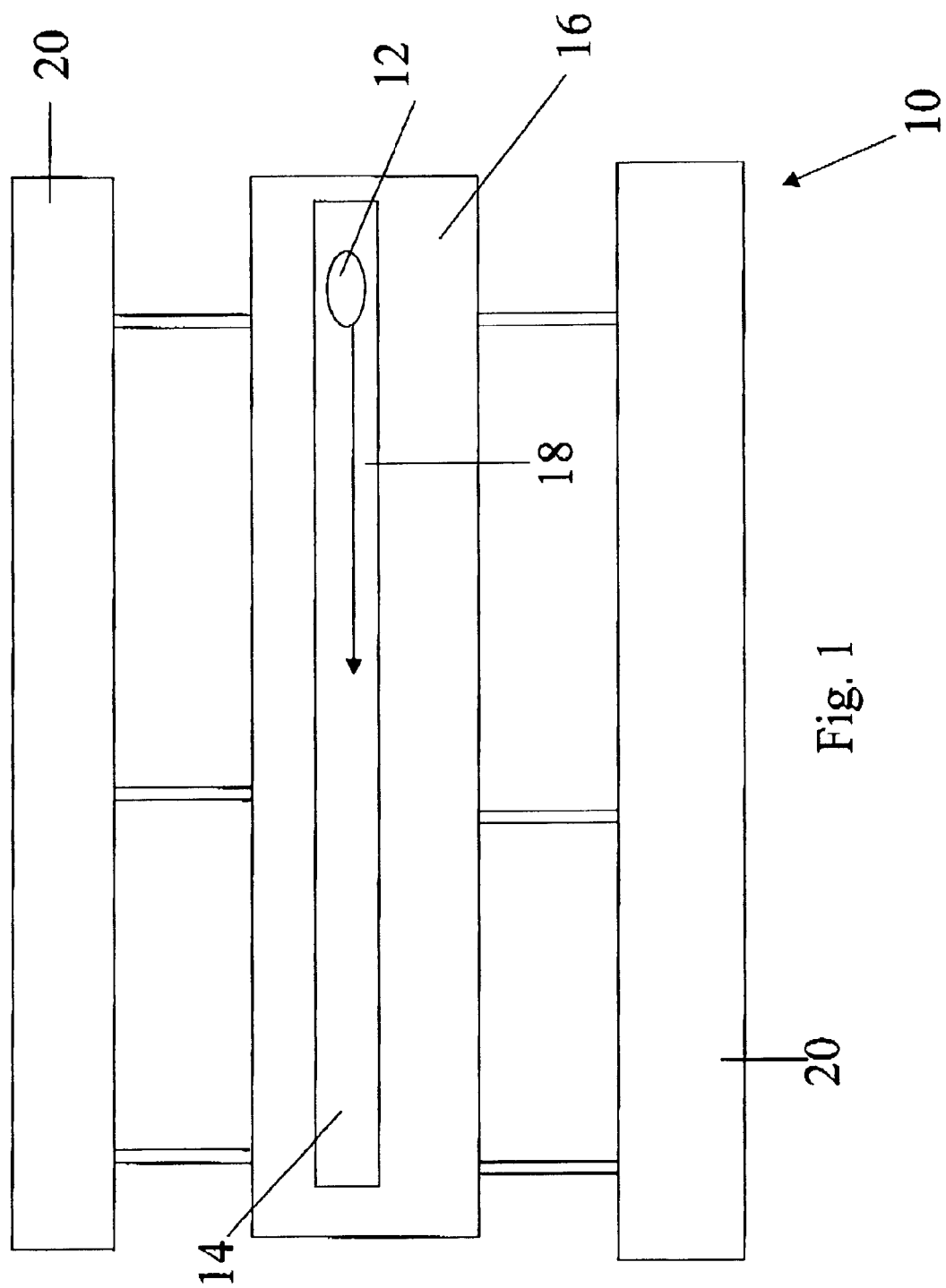
FIG. 1 is a simplified diagram showing a vehicle underside inspection system according to a first preferred embodiment of the present invention.

The present embodiments comprise a controllably movable imaging device mounted on a camera track. The track may be floor mounted to allow vehicles to be driven over it and may further include an illumination source. The imaging device, preferably a still or video camera, may be scanned along a vehicle underside as an operator views the resulting images on a screen. The imaging device is preferably sealed under laminated glass to protect from environmental hazards. The camera track may be mounted between vehicle guide trucks.

The principles and operation of a controllably movable imaging device mounted on a camera track according to the present invention may be better understood with reference to the drawings and accompanying description.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Referring now to the drawings, FIG. 1 illustrates a limited access space inspection system. The inspection system 10 comprises an imaging device 12 for imaging a region in the limited access space. The imaging device 12 is mounted on a track 14 within a track mounting 16. The imaging device 12 is linearly movable along the track 14 in the direction of arrow 18 and is preferably also able to rotate about the track and about an axis perpendicular to the track, the latter at 360°, with the help of controllable actuators. In a preferred embodiment the imaging device is a dome-mounted camera system, such as the Sivis Mini Dome System 3 marketed by Siemens GmbH of Munich, Germany. Such a dome system automatically provides numerous camera movement features such as rotation, tilt, pan, zoom-in, zoom-out and the like and is fully programmable.

The camera is preferably a standard black and white or color still or video camera. In a preferred embodiment the camera is able to alternate between black and white and color modes. Alternatively, depending on what the system is being used to monitor, infra-red or x-ray or other radiation detectors may be used.

The track mounting 16 is preferably located between vehicle guide tracks 20 to allow a vehicle to position itself above the imaging device 12. The track mounting is preferably designed to be inserted into the floor so that a vehicle simply has to drive onto the vehicle guide tracks to provide the imaging device with a clear view of the underside of the vehicle.

Figure 2:
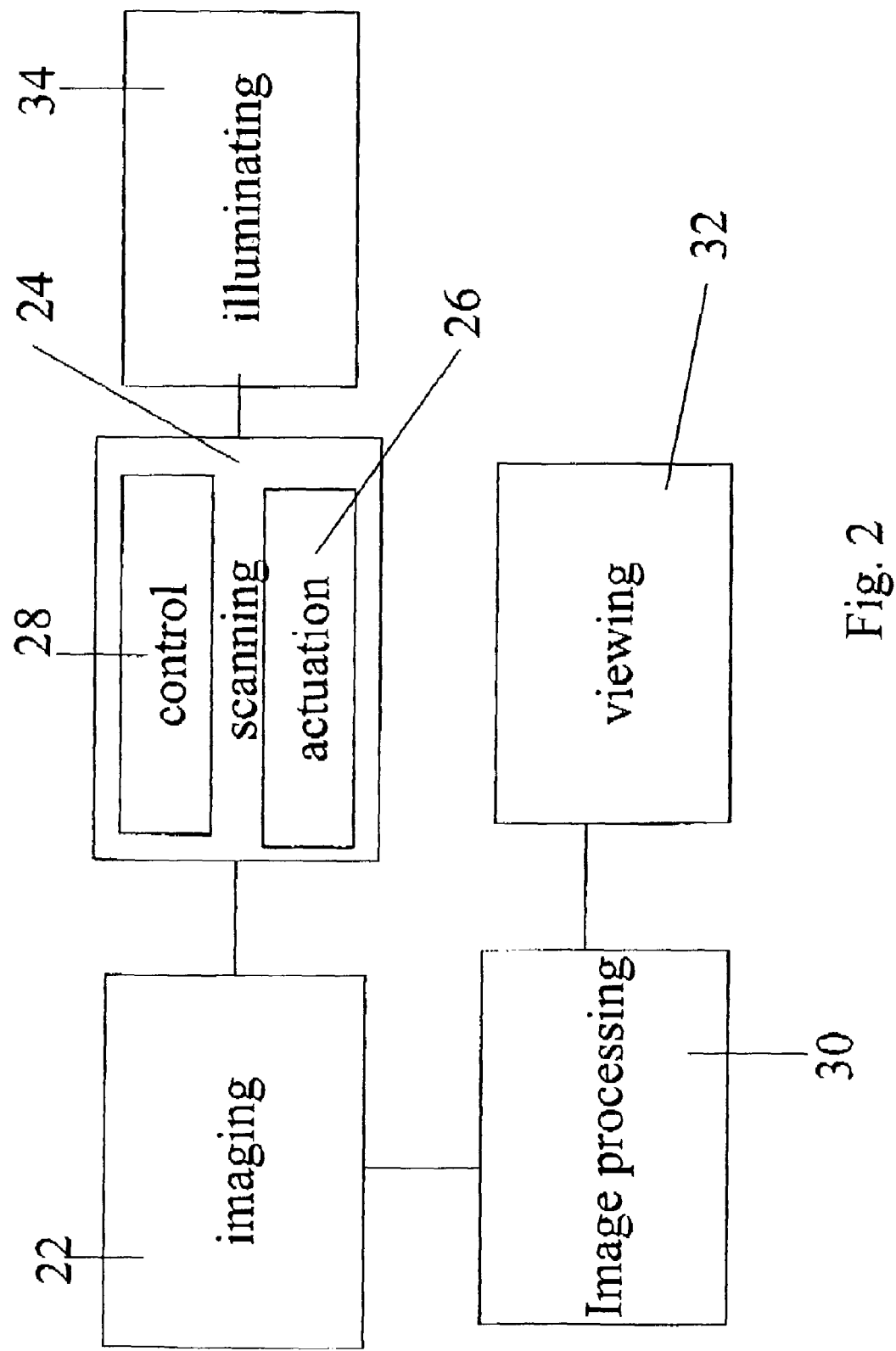
FIG. 2 is a simplified block diagram showing electronic subsystems of the vehicle underside inspection system of FIG. 1.

Reference is now made to FIG. 2, which is a simplified block diagram showing the various electronic subsystems of the inspection system of FIG. 1. An imaging subsystem 22 comprises a camera or other imaging device and associated imaging electronics. A scanning subsystem 24 comprises a scanning control subsystem 26 and an actuation subsystem 28. The actuation subsystem moves the camera through linear and rotary motion in accordance with instructions from the scanning control subsystem. The scanning control subsystem controls the camera to scan the vehicle underside, either according to a pre-recorded program or according to instructions received from the user or operator as he views the output on a screen.

An image processing subsystem 30 carries out various image-processing operations additional to those that a typical camera may normally provide. For example it may increase contrasts, use an overall lighting level to select between color and black and white modes, and in a particularly preferred embodiment may carry out alignment between a current image and a stored image and then carry out a comparison in order to detect differences between the two images. Such a comparison is useful for mechanical inspections of the same vehicle. That is to say an inspection of a given vehicle may be compared with an earlier inspection of the same vehicle so as to detect the appearance of cracks or the development of existing cracks. In automated security comparison may be made with a stored image of the same type of vehicle so as to highlight obvious differences such as the insertion of an explosive device.

A viewing subsystem 32 takes output either directly from the imaging subsystem 22 or from the image processing subsystem 30 and displays it. The viewing subsystem 22 may use any kind of visual display unit. An illumination subsystem 34 preferably comprises a light or other illumination source, which preferably moves along with the imaging device 12. If a radiation detector for radiation other than light is used then the illumination source is selected accordingly.

Figure 3:
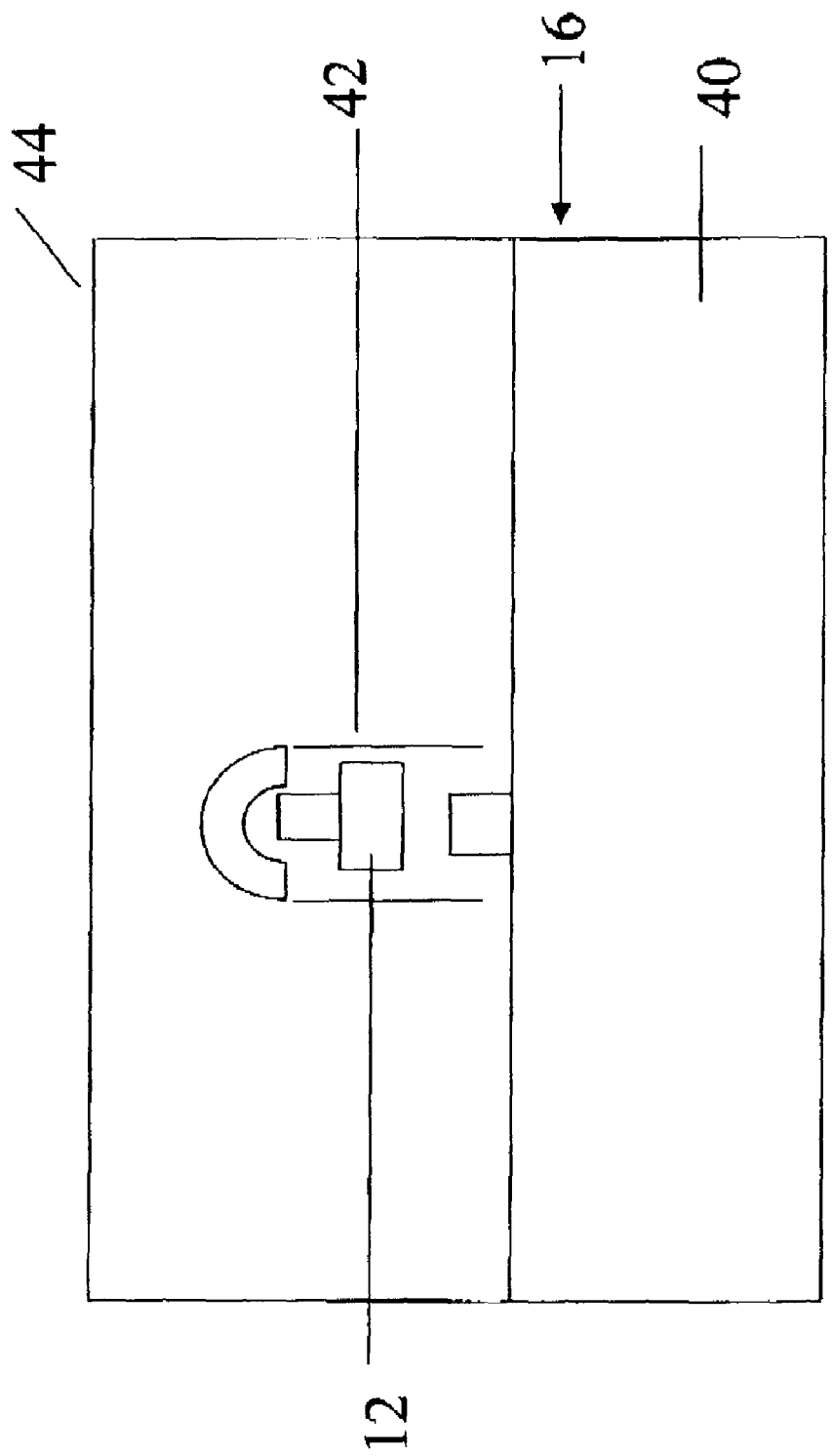
FIG. 3 is a simplified cross section of the vehicle underside inspection system of FIG. 1.

Reference is now made to FIG. 3, which is a simplified cross-section of the track mounting 16 of FIG. 1. Track mounting 16 comprises a base 40 upon which is mounted camera track 14. Camera track 14 may be toothed along its length to improve traction and accuracy of the actuation system. The imaging device 12 is preferably mounted within a dome construction 42, as described above. Track mounting 16 further comprises a protective housing 44 for protecting the imaging device from the environment. The protective housing preferably seals the imaging device and supporting electronics from the external environment. At the very least the protective housing interposes between the imaging device and the region to be imaged thus protecting the imaging device from oil spillage knocks and other hazards.

Preferably, the protective housing comprises a transparent region located between the imaging device and the region to be imaged. In an embodiment, the transparent region comprises laminated glass, and in a prototype triplex laminated glass of 22 mm thickness was used.

Preferably, the mounting is a floor mounting for mounting the imaging device at floor level. In a particularly preferred embodiment, the mounting is a flush floor mounting for insertion into a floor cavity.

Figure 4:
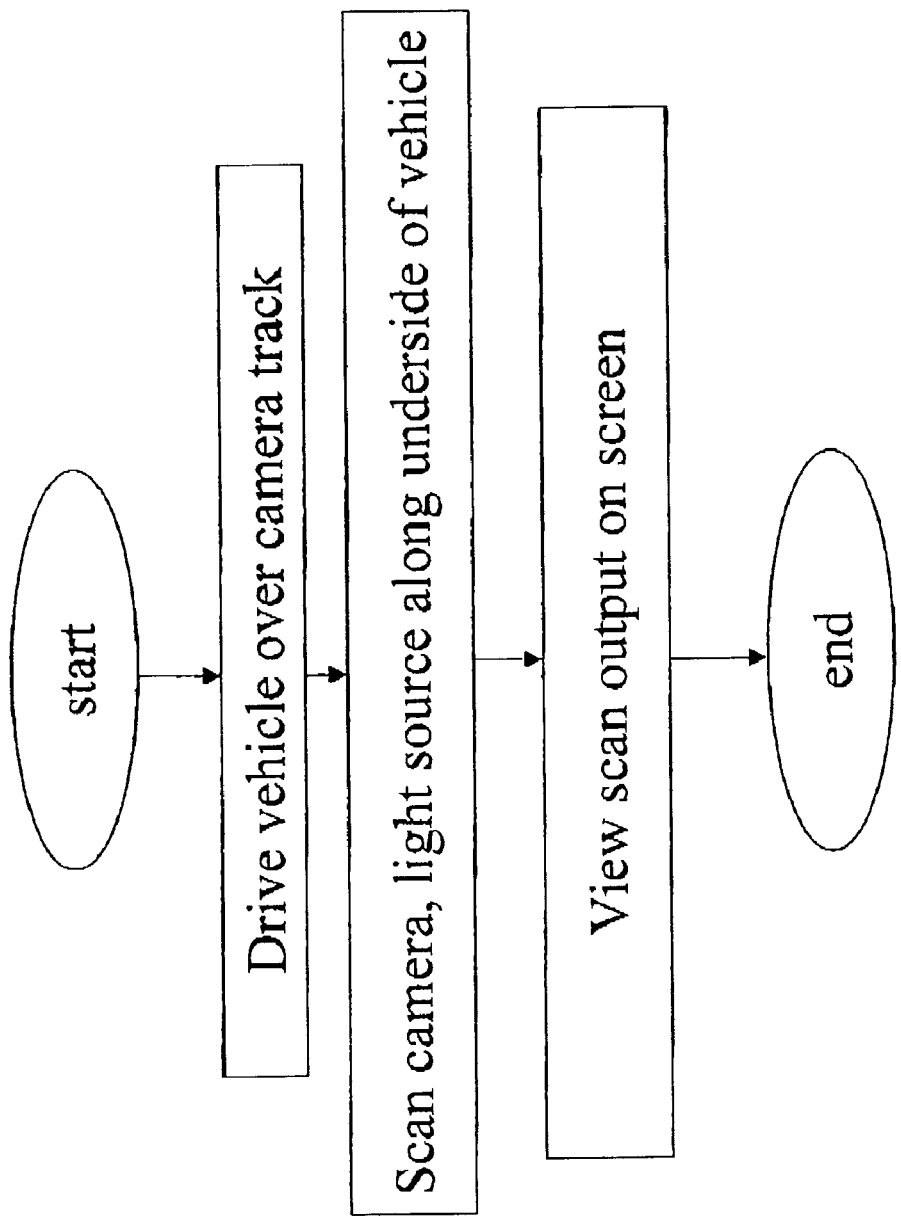
FIG. 4 is a flow chart showing a first embodiment of operation of the system of FIG. 1.

Reference is now made to FIG. 4, which is a simplified flow chart showing operation of a preferred embodiment of the present invention. In FIG. 4 a vehicle is driven onto a rail carrying an imaging device. The invention is not however restricted to "drive-on" inspection of vehicles and thus, as an alternative, it is possible to insert a rail carrying an imaging assembly into any kind of space that it is difficult to access and then to operative the assembly to scan the space. In either case, the imaging device then scans the space, either under control of a program or according to instructions from an operator. The output is viewed and the operator decides whether any kind of action is necessary. The output may additionally he recorded if desired.

Figure 5:
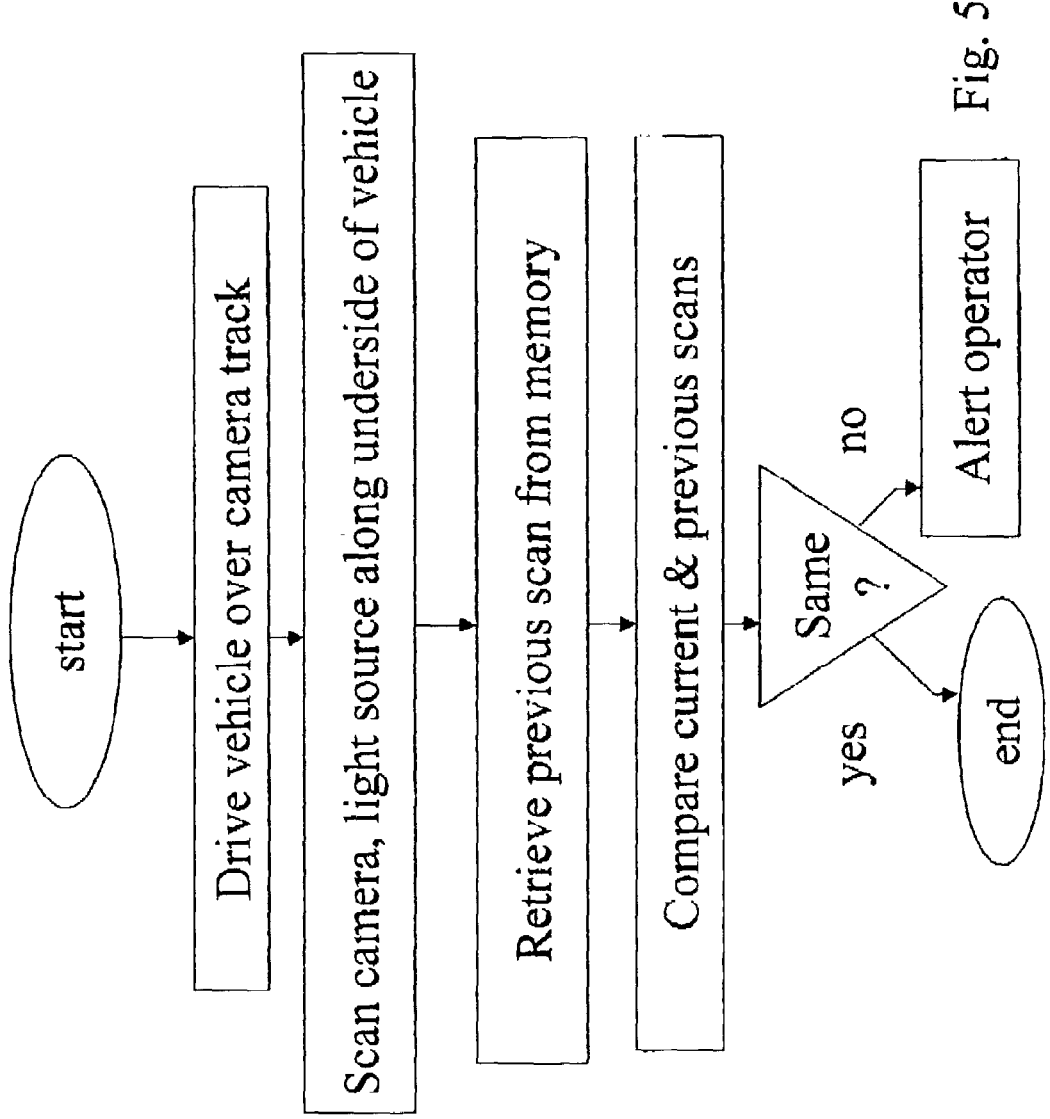
FIG. 5 is a flow chart showing a second embodiment of operation of the system of FIG. 1.

Reference is now made to FIG. 5, which is a flow chart showing operation according to an alternative embodiment of the present invention. Stages that are identical to those of FIG. 4 are not described again except as necessary for an understanding of the present embodiment. In FIG. 5 the positioning and scanning stages are the same. However at that point a previous scan of the same vehicle or same kind of vehicle is retrieved if available and a comparison is carried out between the two scans. The operator is then alerted regarding any differences.

Figure 6:
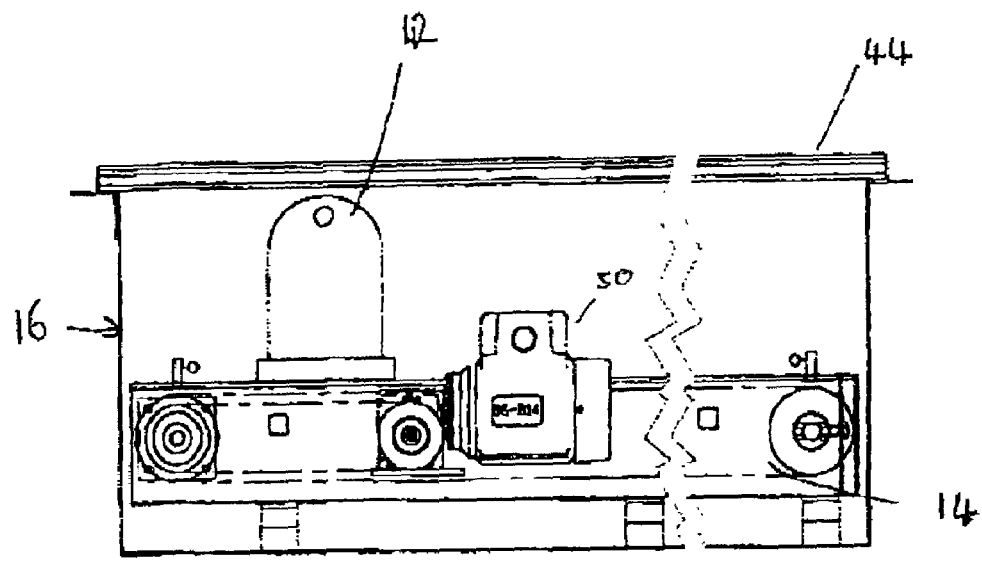
FIG. 6 is a schematic diagram showing assembly details of a prototype embodiment of the present invention viewed from the side.
Figure 7:
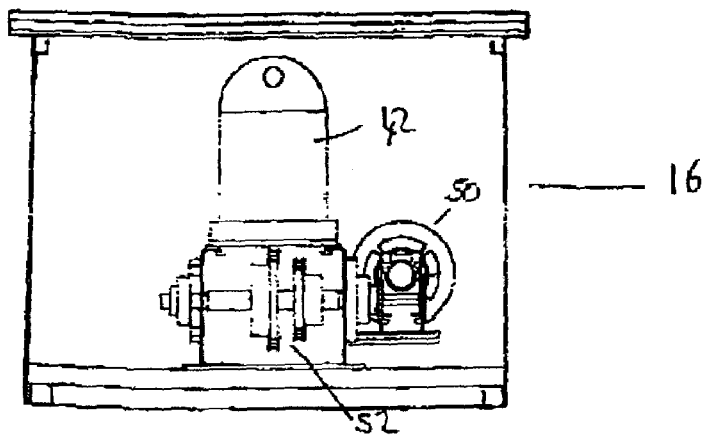
FIG. 7 is a schematic diagram showing assembly details of the same prototype as viewed along the direction of the track.

Reference is now made to FIG. 6, which is a simplified schematic diagram showing assembly details of a prototype embodiment of part of an inspection system according to the present invention viewed from the side. Reference is simultaneously made to FIG. 7 which shows the same assembly viewed along the direction of the rail. Parts that are the same as in previous figures are given the same reference numerals and are not described again except to the extent necessary for an understanding of the present figure. The dome construction 42 is located on track 14 which itself is located on track mounting 16. A motor 50 is provided alongside the dome construction 42 to provide the dome construction with traction to run along the track 14. The motor 50 powers toothed pulleys 52, which intermesh with a toothed central runway of the track 14, thereby to provide the traction.

It is expected that during the life of this patent many relevant imaging devices and systems will be developed and the scope of the terms herein, particularly of the terms "camera" and "imaging system", is intended to include all such new technologies a priori.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

It is appreciated that curtain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A limited access space inspection system for inspecting by scanning instances of a predetermined set of defined limited access spaces, the system comprising:

an imaging device for imaging a region in any one of said defined limited access spaces, said limited access spaces comprising inwardly reaching recesses, a mounting for movably mounting said imaging device to be scannable through linear and rotary motion about said inwardly reaching recesses of limited access spaces and a scanning control unit, associated with said imaging device, configured to control said imaging device to scan about said inwardly reaching recesses of said limited access spaces according to a selected one of respective pre-recorded programs, said program selectable for said instance within said set and comprising instructions for moving said imaging device linearly along a track, for rotating said imaging device about an axis perpendicular to said track, and for rotating said imaging device about an axis parallel to said track, thereby to navigate said imaging device about said inwardly reaching recesses of said limited access spaces, thereby to configure said scan for said instance.

2. The system of claim 1, further comprising a protective housing for protecting said imaging device from the environment by interposing between at least said imaging device and said region to be imaged.

3. The system of claim 2, wherein said protective housing comprises a transparent region located between said imaging device and said region to be imaged.

4. The system of claim 3, wherein said transparent region comprises laminated glass.

5. The system of claim 4, wherein said laminated glass is triplex laminated glass.

6. The system of claim 1, wherein said mounting is a floor mounting for mounting said imaging device at floor level.

7. The system of claim 6, wherein said mounting is a flush floor mounting for insertion into a floor cavity.

8. The system of claim 1, wherein said mounting comprises a camera track for movably bearing said imaging device.

9. The system of claim 8, wherein said imaging device is linearly movable along said camera track, is rotatable about an axis perpendicular to said track, and is further rotatable about an axis parallel to said track.

10. The system of claim 9, wherein said scanning control unit is controllable by at least one of direct user input and by preprogramming, to scan said imaging device about said limited access space.

11. The system of claim 1, wherein said mounting comprises guide tracks for guiding a vehicle thereover, an underside of said vehicle thereby forming said limited access space.

12. The system of claim 1, further comprising an illumination source for providing illumination to said limited access space.

13. The system of claim 1, further comprising a display output for providing a display signal.

14. The system of claim 13, further comprising an image processor, located between said imaging device and said display output to process images from said imaging device prior to output.

15. The system of claim 14, wherein said image processor is operable to compare a current image of said region with a previous image to detect differences therebetween.

16. The system of claim 1, wherein said imaging device is configured to scan about said limited access space according to preprogrammed instructions input to said scanning control unit.

17. The system of claim 16, configured such that said instructions vary depending on vehicle type.

18. A vehicle underside inspection system for inspecting by scanning instances of a predetermined set of defined limited access spaces, the system comprising:

a floor mounted track, an imaging device to be scannable through linear and rotary motion mounted on said floor track;

a scanning control unit, associated with said imaging device, configured to control said imaging device to scan about said vehicle underside, said vehicle underside comprising inwardly reaching recesses, according to a pre-recorded program, said program being variable between vehicle type and comprising instructions for moving said imaging device to scan said inwardly reaching recesses, said moving comprising motions linearly along a track, motions for rotating said imaging device about an axis perpendicular to said track, and motions for rotating said imaging device about an axis parallel to said track, said program thereby configuring said scan for specific vehicle type; and a display output, associated with said imaging device, for providing a display signal of output of said imaging device.

19. The system of claim 18, further comprising a scanning controller for controlling said imaging device to scan an imaging region over said floor track.

20. The system of claim 19, wherein said imaging device is rotatable about an axis perpendicular to said floor track, and is further rotatable about an axis parallel to said floor track.

21. The system of claim 18, wherein said floor mounted track comprises an outer housing and wherein said imaging device is sealed within said outer housing.

22. A method of scanning a limited access space of a set of differently configured spaces, the limited access space having inwardly reaching recesses, the method comprising:

preprogramming a linear track into each of said spaces of said set, thereby to provide specific scanning program for each space of said set, said linear track having an imaging device movably mounted thereon, said linear track being selected to probe said inwardly reaching recesses, and moving said imaging device along said track, according to said specific scanning program, thereby to scan said space through linear and rotary motion, wherein said preprogramming is carried out using instructions for moving said imaging device linearly along said track, instructions for rotating said imaging device about an axis perpendicular to said track, and instructions for rotating said imaging device about an axis parallel to said track.

23. The method of claim 22, wherein said preprogramming said linear track into said space comprises locating a vehicle over said track, an underside of said vehicle forming said limited access space.

24. The method of claim 23, wherein said linear track is flush with a floor.

25. The method of claim 22, further comprising interpolating an illumination source into said space.

* * * * *